United States Patent [19]

El-Fakahany

[11] Patent Number: 4,797,410

[45] Date of Patent: Jan. 10, 1989

[54] SUPPRESSION OF WITHDRAWAL SYMPTOMS IN OPIOID-INDUCED TOLERANCE OR DEPENDENCE

[75] Inventor: Esam E. El-Fakahany, West Minster, Md.

[73] Assignee: Miles Inc., Elkhart, Ind.

[21] Appl. No.: 40,755

[22] Filed: Apr. 16, 1987

Related U.S. Application Data

[63] Continuation of Ser. No. 733,664, May 13, 1985, abandoned.

[51] Int. Cl.$^4$ .................... A61K 31/44; A61K 31/275; A61K 31/135
[52] U.S. Cl. .................................... 514/356; 514/523; 514/654; 514/812
[58] Field of Search ................ 514/812, 356, 523, 654

[56] References Cited

PUBLICATIONS

*Calcium Blockers*, Flaim et al, Urban & Schwarzenberg, Baltimore–Munich, 1982, pp. 186–189, 196 & 197.

*Primary Examiner*—Frederick E. Waddell
*Attorney, Agent, or Firm*—E. P. Gray; M. G. Boguslaski

[57] ABSTRACT

A method for suppressing withdrawal symptoms in an opioid-induced tolerant or physically dependent individual is disclosed. The method comprises administering to such individual an effective amount of a calcium channel blocking drug or pharmaceutically acceptable non-toxic salt thereof to suppress said withdrawal in said individual. Also disclosed are pharmaceutical compositions suitable for use in suppressing withdrawal symptoms in an opioid-induced tolerant or physically dependent individual.

6 Claims, No Drawings

SUPPRESSION OF WITHDRAWAL SYMPTOMS IN OPIOID-INDUCED TOLERANCE OR DEPENDENCE

This is a continuation, of application Ser. No. 733,664, filed May 13, 1985, now abandoned.

BACKGROUND OF THE INVENTION

Morphine and related opioids produce their major effects on the central nervous system and bowel. The effects of these compounds are diverse and include analgesia, drowsiness, changes in mood, respiratory depression, decreased gastrointestinal motility, nausea, vomiting, and alterations of the endocrine and autonomic nervous systems. Much research in the field of opioid pharmacology has focused on the understanding of the molecular nature of the phenomena of tolerance and physical dependence attendant to prolonged medical treatment with these compounds as well as the non-medical use thereof (such as in compulsive drug use or compulsive drug abuse).

Calcium has been hypothesized to play an important role in morphine-induced analgesia possibly due to the ability of morphine to inhibit calcium movement in nerve terminals (Kaimkubo et al, *European Journal of Pharmacology*, Vol. 95, p. 149, 1983). Some evidence is available which may tend to support this hypothesis. For example, in "Methods in Psychobiology", Vol. 2, pp. 155 et seq (1972), Weeks has described the ability of calcium channel blockers to produce morphine-like analgesia and Kakunaga et al (*J. Pharmacol. Exp. Ther.*, 153, p. 134, 1966) describe their findings that calcium ions and calcium ionophores can elicit hyperalgesia. Additionally it has been reported that chronic treatment with opioids results in an increase in potassium-stimulated calcium uptake in brain synaptosomes (*Calcium in Drug Action*, J. B. Weiss, Editor, pp. 241 et seq, Plenum Press, New York, 1978). However, none of the research in opioid pharmacology has suggested that calcium channel blocking drugs may be useful in suppressing withdrawal symptoms in opioid-induced tolerant or physically dependent individuals.

SUMMARY OF THE INVENTION

The present invention is directed to a method for suppressing withdrawal symptoms in an opioid-induced tolerant or physically dependent individual comprising administering to said individual an effective amount of a calcium channel blocking drug or a pharmaceutically acceptable non-toxic salt thereof to suppress said withdrawal in said individual. Also disclosed are pharmaceutical compositions suitable for use in suppressing withdrawal symptoms in an opioid-induced tolerant or physically dependent individual containing an effective amount of a calcium channel blocking drug or a pharmaceutically acceptable non-toxic salt thereof in combination with a pharmaceutically acceptable non-toxic inert diluent or carrier.

DETAILED DESCRIPTION OF THE INVENTION

As described earlier, a common adjunct to the medical or non-medical use of opioids is the induced tolerance and physical dependence which develops as a result of either controlled or indiscriminate use of these compounds. The development of tolerance and physical dependence with repeated use is characteristic of all opioids. Precise definitions for the terms "tolerance" and "physical dependence" are difficult to make owing to the vast amount of literature describing the medical and non-medical (i.e., abusive) uses for the opioids and differing opinions of the writers as to what is to be circumscribed within the meaning of each term. Suffice it to say that for present purposes the term "tolerance" refers to a progressive diminution of susceptibility to the effects of an opioid resulting from its continued administration at a constant dose. "Physical dependence" refers to the perceived need developed by an individual for the continued administration of an opioid to prevent the development of the physiological disturbances known as "abstinence syndrome" or simply withdrawal. Similarly the term "withdrawal" is not susceptible of precise definition but may best be looked at in terms of the myriad symptoms accompanying abstinence from an opioid. Such symptoms include sympathetic effects such as lacrimation, rhinorrhea, sweating, piloerection, dilated pupils, elevated blood pressure and pulse rate as well as parasympathetic manifestations such as emesis, abdominal pain and diarrhea. Behavioral hyperexcitability may be observed in terms of anxiety, restlessness, yawning, tremor or insomnia and additionally muscle and joint pain will ensue. These definitions are provided as guides to an understanding of the discussions provided herein, recognizing that precise definitions are not critical to the method of the present invention and that differences of opinion may exist as to what is meant by each term.

Jaffe and Martin in *The Pharmacological Basis of Therapeutics*, Sixth Edition, pp. 494 et seq (1980) define the term "opioid" as referring to a generic designation for all exogenous substances that bind specifically to any of several subspecies of opioid receptors and produce some agonistic action. Hence, the term "opioid" is used herein in its broadest pharmacologic sense as referring to the naturally occurring alkaloids of opium such as morphine or codeine as well as synthetic or semi-synthetic variants thereof. Such compounds include (in addition to morphine and codeine) for example, diacetylmorphine (heroin), dihydroxymorphinone, dihydromorphinone, methyldihydromorphinone, dihydrocodeine, hydrocodone, oxycodone and the like. Other such compounds include methadone, propoxyphene, meperidine and other phenylpiperidines such as anileridine, alphaprodine or diphenoxylate; morphinans such as levorphanol, methorphan, levallorphan; and benzomorphans such as phenazocine or pentazocine.

The calcium channel blocking drugs which may be used in the method and pharmaceutical compositions of the present invention include the 1,4-dihydropyridines such as nitrendipine, nifedipine, nimodipine, nisoldipine and the like; β-phenethylamines such as tiapamil and verapamil; benzothiazepines such as diltiazem; ethylenediamines such as bepridil; and diaryl alkyl amines such as lidoflazine, prenylamine, fendiline, terodiline, cinnarizine and flunarizine. Of the calcium channel blocking drugs which may be used in the present invention, the 1,4-dihydropyridines and the β-phenethylamines are preferred. Of the 1,4-dihydropyridines, nisoldipine, nifedipine and nimodipine are particularly preferred for use in the method and pharmaceutical compositions of the present invention. Nisoldipine is isobutyl methyl 1,4-dihydro-2,6-dimethyl-4-(2-nitrophenyl)-3,5-pyridinecarboxylate. Nifedipine is 3,5-pyridinecarboxylic acid, 1,4-dihydro-2,6-dimethyl-4-(2-nitrophenyl)-dimethyl ester. Nimodipine is 1,4-dihydro- 2,6-dimethyl-4-(3'-nitrophenyl)-pyridine-3-(β-methoxyethyl ester)-5-isopropyl ester. Of the β-phenethylamines, verapamil is particularly preferred for use in the method and pharamceutical compositions of the present invention. Verapamil is 5-[(3,4-dimethoxyphenethyl)-methylamino]-2-(3,4-dimethoxyphenyl)-2-isopropyl-valeronitrile.

For purposes of the present invention an effective amount of a calcium channel blocking drug or a combination of one or more calcium channel blocking drugs is administered. As used herein, the term "effective amount" refers to that amount of one or a combination of one or more calcium channel blocking drugs necessary to suppress withdrawal symptoms in an opioid-induced tolerant or physically dependent individual. The skilled artisan will readily appreciate that the effective dosage ranges for the various calcium channel blocking drugs used in the methods and compositions of the present invention will vary widely particularly where the route of administration and the precise drug to be used are considerations. Of course other factors such as the size and age of the patient as well as the time and frequency of administration are to be considered in determining the dose in a given situation. Suffice it to say that the precise dose to be administered in a particular case will be either readily known from the published literature or can be determined by conventional dose titration techniques. Typically though not necessarily the dosages may range anywhere from about 0.0001 milligram (mg) per kilogram (kg) of body weight per day to about 100 mg per kg of body weight per day. For example, for the specific compound nimodipine the dose for intravenous administration may fall anywhere within the range of from about 0.0001 mg per kg of body weight per day to about 0.5 mg per kg, preferably from about 0.001 to about 0.1 mg per kg of body weight per day. For oral administration the dose may fall anywhere within the range of from about 0.001 mg per kg of body weight per day to about 1 mg per kg of body weight per day, preferably from about 0.01 to about 0.5 mg per kg of body weight per day.

The calcium channel blocking drug is administered internally in the form of a pharmaceutical composition comprising one or more of said calcium channel blocking drugs or pharmaceutically acceptable non-toxic salts thereof in admixture with one or more pharmaceutically-acceptable non-toxic diluents or carriers, i.e., a diluent or carrier which is chemically inert to the drug and which has no detrimental side effects or toxicity under the conditons of use. Internal administration of the compounds may be parenteral as for example by intraperitoneal, subcutaneous intramuscular or intravenous injection. Dosage forms for parenteral administration can be prepared by suspending or dissolving an amount of the calcium channel blocking drug in a non-toxic liquid vehicle suitable for injection such as an aqueous or oleaginous medium and sterilizing the suspension or solution. Alternatively, a measured amount of the drug may be placed in a vial and the vial and its contents sterilized and sealed. An accompanying vial or vehicle can be provided for purposes of mixing prior to administration. Pharmaceutical compositions adapted for parenteral administration employ diluents and carriers such as water and water-miscible organic solvents such as sesame oil, groundnut oil, aqueous propylene glycol and N,N'-dimethylformamide. Examples of such pharmaceutical compositions include sterile, isotonic, aqueous saline solutions of the calcium channel blocking drug which can be buffered with a pharmaceutically acceptable buffer and which are pyrogen free.

Internal administration of the calcium channel blocking drug may also be accomplished by means of oral pharmaceutical dosage forms. These include any of the conventional solid or liquid dosage forms such as powders, tablets, capsules, suspensions, solutions, syrups and the like including any sustained release preparations of the above. Such oral pharmaceutical dosage forms employ such ingredients as diluents and carriers, excipients and lubricants such as glucose, lactose, sucrose, corn and potato starch, sodium carboxymethylcellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, dicalcium phosphate; as well as various buffering agents, surfactants, emulsifiers, dispersing agents, flavoring agents and the like.

Preparation of the pharmaceutical compositions described herein may be readily achieved by one skilled in the art. Further information pertinent to the preparation of such compositions may be obtained by reference to standard treatises such as *Remington's Pharmaceutical Sciences*, Sixteenth Edition, Mack Publishing Co., Easton, PA (1980).

The following examples are provided as a means of illustrating the present invention and are not to be construed as a limitation thereon.

EXAMPLE 1

Male ICR mice were made tolerant to morphine by the subcutaneous implantation of a morphine pellet (75 mg, morphine base) which was maintained in the animal for three days. These mice were then divided into two groups. One group was injected (intraperitoneally) with 16.6 mg/kg of nisoldipine while the second group was maintained as a control (no nisoldipine was administered). Withdrawal was precipitated in both groups of mice by the intraperitoneal injection of 0.5 mg/kg of naloxone 15 minutes after nisoldipine administration. Naloxone is a narcotic antagonist capable of inducing withdrawal symptoms in opioid-tolerant states. The naloxone withdrawal was evidenced by episodes of jumping and the number of jumps for each mouse in each group were determined for a five minute period. The group of mice pretreated with nisoldipine exhibited an approximately 61 percent decrease in naloxone-precipitated jumping relative to the control group.

EXAMPLE 2

Following substantially the same procedure as described in Example 1, three groups of morphine tolerant male ICR mice were pretreated with two different doses of nimodipine prior to administration of the naloxone. The nimodipine was found to inhibit the naloxone-precipitated jumping by about 43 percent and 65 percent at doses of 5 and 10 mg/kg of nimodipine, respectively (percent inhibition all relative to control where no nimodipine was administered).

EXAMPLE 3

Male Sprague-Dawley rats were made morphine-tolerant by chronic intraperitoneal injections of morphine as follows. On the first day, rats were given three 10 mg/kg doses of morphine at four hour intervals. The dose of morphine was increased on successive days to 20 and 50 mg/kg three times daily and then to 100 mg/kg three times daily for two days and finally to 200 mg/kg three times daily for one day. One group of these rats was then administered (intraperitoneally) 20 mg/kg of nisoldipine and a second group was maintained as a control (i.e., no nisoldipine was given). Fifteen minutes after the nisoldipine was administered, withdrawal was precipitated in each group by the intraperitoneal injection of 0.5 mg/kg naloxone. Both groups of rats were then scored during the 30 minute period immediately following naloxone injection for withdrawal signs of abdominal stretching, diarrhea, "wet dog" shakes, teeth chattering, ptosis and weight loss. The results of this study are shown in Table I.

TABLE I

Effect of Nisoldipine (20 mg/kg) on Naloxone-induced Withdrawal Signs in Morphine Tolerant Rats[a]

| Withdrawal Signs | Animal Number | | | | | | |
|---|---|---|---|---|---|---|---|
| | Control | | | Nisoldipine Pretreated | | | |
| | 1 | 2 | 3 | 4 | 5 | 6 | 7 |
| Abdominal Stretching | + | 0 | + | + | 0 | 0 | 0 |
| Diarrhea | + | + | + | 0 | 0 | 0 | 0 |
| "Wet dog" Shakes | + | + | 0 | 0 | 0 | 0 | 0 |
| Teeth Chattering | + | + | + | + | 0 | 0 | 0 |
| Ptosis | + | + | + | + | + | + | + |

[a] "+" means the withdrawal sign is present;
"0" means the withdrawal sign is absent The data shown in Table I clearly indicate that nisoldipine was effective in suppressing four out of the five withdrawal symptoms observed for those pretreated animals.

EXAMPLE 4

The procedure set forth in Example 3 was repeated using nimodipine (10 mg/kg) rather than nisoldipine. The results are shown in Table II.

TABLE II

Effect of Nimodipine (10 mg/kg) on Naloxone-induced Withdrawal Signs in Morphine Tolerant Rats[a]

| Withdrawal Signs | Animal Number | | | | | |
|---|---|---|---|---|---|---|
| | Control | | | Nimodipine Pretreated | | |
| | 1 | 2 | 3 | 4 | 5 | 6 |
| Abdominal Stretching | + | + | + | 0 | 0 | 0 |
| Diarrhea | + | + | + | 0 | 0 | 0 |
| "Wet dog" Shakes | + | + | + | 0 | + | 0 |
| Teeth Chattering | + | + | + | + | + | + |
| Ptosis | + | + | + | 0 | + | 0 |

[a] "+" means the withdrawal sign is present;
"0" means the withdrawal sign is absent The data shown in Table II clearly indicate that nimodipine was effective in suppressing four out of the five withdrawal symptoms observed for those pretreated animals.

EXAMPLE 5

Two groups of rats were made tolerant to morphine as described in Example 3. A third nontolerant group was maintained as a control. Nifedipine (20 mg/kg) was administered (intraperitoneally) to one of the groups of morphine-tolerant rats and 15 minutes later naloxone (1 mg/kg) was administered to all three groups of rats. Each group of rats was observed and evaluated for diarrhea and subsequent body weight loss associated with withdrawal. The group of morphine tolerant rats pretreated with nifedipine was found to show no weight loss relative to the nontolerant control for the three hour period immediately following naloxone injection. An approximately 10 percent weight loss (relative to the nontolerant control) was measured for the group of rats made tolerant but not pretreated with nifedipine.

This same procedure was repeated using nimodipine (10 mg/kg) instead of nifedipine. The group of morphine tolerant rats pretreated with nimodipine was found to show an approximate 2 percent weight loss relative to the nontolerant control for the three hour period immediately following naloxone injection. An approximately 10 percent weight loss (relative to the nontolerant control) was measured for the group of rats made tolerant but not pretreated with nimodipine.

EXAMPLE 6

The procedure set forth in Example 5 was repeated using verapamil (10 mg/kg) as the calcium channel blocking drug. The group of morphine tolerant rats pretreated with verapamil was found to show an approximate 3 percent weight loss relative to th nontolerant control for the three hour period immediately following naloxone injection. An approximately 10 percent weight loss (relative to the nontolerant control) was measured for the group of rats made tolerant but not pretreated with verapamil.

What is claimed is:

1. A method for suppressing withdrawal symptoms in an opioid-induced tolerant or physically dependent individual, said withdrawal symptoms selected from the group consisting of:
   (a) the sympathetic effects of lacrimation, rhinorrhea, sweating, piloerection, dilated pupils and elevated pulse rate;
   (b) parasympathetic effects;
   (c) behavioral hyperexcitability;
   (d) muscle and joint pain; and
   (e) ptosis,
said method comprising administering to said individual an effective amount of a 1,4-dihydropyridine calcium channel blocking drug or a pharmaceutically acceptable non-toxic salt thereof to suppress said withdrawal symptoms in said individual.

2. A method for suppressing withdrawal symptoms in an opioid-induced tolerant or physically dependent individual, said withdrawal symptoms selected from the group consisting of:
   (a) the sympathetic effects of lacrimation, rhinorrhea, sweating, piloerection, dilated pupils and elevated pulse rate;
   (b) parasympathetic effects;
   (c) behavioral hyperexcitability;
   (d) muscle and joint pain; and
   (e) ptosis,
said method comprising administering to said individual an effective amount of a β-phenethyl-amine calcium channel blocking drug or a pharmaceutically acceptable non-toxic salt thereof to suppress said withdrawal symptoms in said individual.

3. The method of claim 1 wherein the 1,4-dihydropyridine calcium channel blocking drug is nisoldipine.

4. The method of claim 1 wherein the 1,4-dihydropyridine calcium channel blocking drug is nifedipine.

5. The method of claim 1 wherein the 1,4-dihydropyridine calcium channel blocking drug is nimodipine.

6. The method of claim 2 wherein the β-phenethylamine calcium channel blocking drug is verapamil.

* * * * *